United States Patent [19]

Schmidt

[11] Patent Number: 5,776,470
[45] Date of Patent: Jul. 7, 1998

[54] METHOD OF USING LIPID TRANSFER PROTEINS AND LIPIDS TO RECONSTITUTE MEMBRANES

[76] Inventor: Karlheinz Schmidt, Aussere Weiler Strasse 12, 7413 Gomaringen, Germany

[21] Appl. No.: 474,460

[22] Filed: Jun. 7, 1995

Related U.S. Application Data

[63] Continuation-in-part of Ser. No. 744,308, Aug. 13, 1991, which is a continuation-in-part of Ser. No. 347,026, May 4, 1989, abandoned.

[30] Foreign Application Priority Data

May 6, 1988 [DE] Germany ............... 38 15 473.0

[51] Int. Cl.$^6$ ............... A61K 7/00; A61K 9/12; A61K 9/127; A61K 9/107
[52] U.S. Cl. ............... 424/401; 424/450; 424/43; 424/44; 424/45; 514/937
[58] Field of Search ............... 424/450, 401, 424/43–45; 514/937–943, 169, 458, 725, 844

[56] References Cited

U.S. PATENT DOCUMENTS

| | | | |
|---|---|---|---|
| 4,812,314 | 3/1989 | Barenholz et al. | 424/450 |
| 5,128,318 | 7/1992 | Levine et al. | 514/2 |

OTHER PUBLICATIONS

Brown, R.E., et al., "Properties of a Specific Glycolipid Transfer Protein From Bovine Brain", *Chemistry and Physics of Lipids*, 38 (1985) 79–83.
Rueckert, Dieter G. and Karlheinz Schmidt, "Lipid Transfer Proteins", *Chemistry and Physics of Lipids*, 56 (1990) 1–20.
Morton, R.E., "Interaction of lipid transfer protein with plasma lipoproteins and cell membranes", *Experientia*, 46 (1990) 552–560.
Voelker, D.R., "Lipid transport pathways in mammalian cells", *Experientia*, 46 (1990) 569–579.
Arondel, V. J.-C. Kader, "Lipid transfer in plants", *Experientia*, 46 (1990) 579–585.
Daum, G. F. Paltauf, "Lipid transport in microorganisms", *Experientia*, 46 (1990) 586–592.
Wirtz, K.W.A. T.W.J. Gadella Jr., "Properties and modes of action of specific and non-specific phospholipid transfer proteins", *Experientia*, 46 (1990) 592–599.

*Primary Examiner*—Gollamudi S. Kishore
*Attorney, Agent, or Firm*—Wigman, Cohen, Leitner & Myers, P.C.

[57] ABSTRACT

Active ingredient system for the lipid exchange with target structures; methods for their manufacture and their use; and products containing active ingredient systems of this type are disclosed. The active ingredient system for the transfer of lipophilic and/or amphophilic components to target structures or from such back to the active ingredient system, as well as to their exchange with the target structures, is formed from at least one lipid component with at least one transfer protein. In the method for the manufacture of the active ingredient system, lipid and protein components are combined into system in different configurations depending on the purpose of its use and its place of use, whereby the specificity results from the lipid used and the transfer protein employed, as well as the direction of the lipid transfer. Active ingredient system of this type are used in technology, such as the material technology, in medicine, pharmaceuticals and in the area of cosmetology. The active ingredient system is present in products such as sprays, gels, cremes or salves.

9 Claims, No Drawings

METHOD OF USING LIPID TRANSFER PROTEINS AND LIPIDS TO RECONSTITUTE MEMBRANES

CROSS-REFERENCE

This application is a C-I-P application of U.S. Ser. No. 07/744,308, filed Aug. 13, 1991, which is a C-I-P of U.S. Ser. No. 07/347,026, filed May 4, 1989, now abandoned, both applications being herein incorporated by reference.

BACKGROUND OF THE INVENTION

1. Field of the Invention

This invention relates to a combination of a lipid transfer protein, a target structure and a lipid depot that can serve as either a source of lipid to be transferred to the target structure or as a depot that can hold lipids transferred from the target structure. In particular, lipid transfer proteins are proteins which exchange or "shuttle" lipophilic and/or amphophilic compounds to and from various target structures, such as cells, tissue, organs, liposomes, micelle, and the like, in order to alter the composition or characteristic of the target structures by, for example, changing its fluidity by adding or removing different lipids, delivering drugs and removing cholesterol, or other lipids.

2. Description of the Prior Art

Until now, lipid exchange between different structures has been accomplished through lipoproteins, vesicular transport, collision, fusion or exchange of soluble monomeric lipid components in an aqueous medium, but these processes proceed very slowly with half-life values measured in hours, so that an efficient and targeted modification of lipid structures is generally not possible with these processes. In addition to the slow kinetics, another significant fact is that other measures to increase the solubility of lipids, such as the use of organic solvents, detergents, high temperatures, etc., often destroy the integrity of the target structure, do not exhibit specificity for the removal or exchange of different lipids and often have undesired side effects when used in vivo.

A number of different people have isolated a number of small, water soluble proteins from extracellular fluids or the intracellular space which have been described as catalyzing the transfer of phospholipids between bilayers and biological membranes. This area was reviewed by K. W. A. Wirtz in *Lipid-Protein Interactions*, pp 151–222, (P. C. Jost and O. H. Griffith Eds.) John Wiley and Sons, New York, 1982 (herein incorporated by reference). Since this review by K. W. A. Wirtz several other reports have described proteins that catalyze the intermembrane transfer of glycolipids including reports by A. Abe et al. in Biochem. Biophys. Res. Commun., 104 (1982) 1386–1393; K. Yamada et al. in Biochim. Biophys. Acta, 687 (1982) 195–203; R. J. Metz et al. in J. Biol. Chem. 255 (1980) 4463–4467; A. Abe et al. in Biochim. Biophys. Acta, 778 (1984) 239–244; M. Wong et al. in Biochemistry, 23 (1984) 6498–6505 and T. Sasaki et a in Biochemistry, 24 (1985) 1079–1083 (all of the above references being herein incorporated by reference).

R. E. Brown et al. in Chemistry and Physics of Lipids, 38 (1985) 79–93 (herein incorporated by reference) describes a glycolipid transfer protein isolated from bovine brain. This protein has a molecular weight of 20,000 daltons and could transfer glycospingolipids and gangliosides including charged species such as $GM_1$ as well as neutral species such as ceramides. The reference teaches that both the donor and acceptor bilayers must be in the liquid crystalline form for transfer to occur.

Others have described a group of lipid transfer proteins called non-specific lipid transfer proteins that have been isolated from rat and bovine liver. These lipid transfer proteins transfer a wide variety of lipids, including cholesterol. Isolation of the lipid transfer protein from rat liver was described by B. Bloj et al. in J. Biol. Chem., 252 (1977) pp 1613–1619, herein incorporated by reference; and isolation of lipid transfer protein from bovine liver was described by R. C. Crain et al. in Biochemistry, 19 (1980) 1433–1439, herein incorporated by reference.

Lipid transfer proteins that catalyze the transfer of cholesterol esters and triglycerides in human serum were isolated by N. M. Pattnaik et al. and described in Biochem. Biophys. Acta, 409 (1978) 393–398. The cholesterol ester lipid transfer protein was cloned and sequenced by D. Drayna et al. and described in Nature 327 (1987) 632–634 herein incorporated by reference. The lipid transfer protein of Drayna was described as having a molecular weight of 62,000 daltons. Lipid transfer proteins have also been isolated from many different plants including maize seedlings (D. Dorady et al. Biochem. Biophys. Acta, 710 (1982) 143–153 herein incorporated by reference and D. Dorady et al. Physiol. Veg. 23 (1985) 373–380 herein incorporated by reference), spinach leaves (J. C. Kader et al. Eur. J. Biochem. 139 (1984) 411–416 and J. C. Kader et al. Meth. Enzymol. 148 (1987) 661–666 both references herein incorporated by reference) and castor bean seedlings (S. Watanabe et al. Biochem. Biophys. Acta, 876 (1986) 116–123 herein incorporated by reference). These lipid transfer proteins have the common property of having a broad specificity for phospholipids such as phosphotidylcholine, phosphotidylinositol and phosphatidylethanolamine. Spinach leaf lipid transfer protein was also shown to be able to bind and transport oleic and linoleic acids as well as oleyl-CoA.

A different lipid transfer system was described that transferred lipids by means of fusing different lipid structures; however, there have been no technically practical lipid transfer systems for the rapid and targeted modification of lipid structures based on the fusion of larger lipid aggregations.

A fusion system is disclosed in PCT/US85/00621 with the publication number WO 85/04880 (hereinafter "PCT reference"), and the term fusion in membrane biophysics includes within its meaning the process of fusing two distinct membranes. A thorough membrane fusion results in the transfer of all the molecules in the membrane, which does not allow a targeted modification of the target structure at the molecular level. It is not possible with the fusion system disclosed in PCT/US85/00621 to transfer molecules that cannot form membranes, such as cholesterol. Furthermore, the membrane proteins mentioned in this reference do not represent lipid transfer proteins, because the membrane proteins are located in the membrane and the lipid transfer proteins are water soluble and are located in the extracellular fluid or intracellular spaces. Moreover, the membrane proteins of this type described in the PCT reference, are inherently incapable of fulfilling a lipid transfer function because of their hydrophobic characteristics do not allow transfer through the extracellular fluids.

In a fusion system according to the PCT reference, only membranes themselves can be used as the lipid component. It is impossible to extract and transfer individual lipid molecules through fusion of the membranes because when the membranes or lipid bilayers fuse all of the lipids are transferred to the new membrane.

U.S. Pat. No. 4,895,719 (hereinafter '719 patent) discloses different kinds of typical drug-carriers where the drugs are encapsulated or entrapped by liposomes. This encapsulation of drugs may be necessary where the drug is known to be rapidly eliminated (metabolized) by the body. An encapsulated drug is released continuously into the blood stream and thus can be effective over a long period of time. According to the '719 patent these drugs can be apolipoproteins or lung surfactant proteins. These proteins are not water soluble transfer proteins and do not possess the lipid transfer catalytic properties. The encapsulation as described in the '719 patent would inhibit any catalytic efficiency of the lipid transfer protein and render it useless for the purposes of the present invention.

DEFINITIONS

The term "transfer" will be used herein to describe the transport of lipid in only one direction, while the term "exchange" will be used for transport of lipid in both directions. The "target structures" referred to can be various lipid structures, such as emulsions, micelles, liposomes, aerosols, single lipid layers, oligolayers, or multilayers of lipid on liquids or solid bodies, or biological systems such as cells, tissues, organs, microorganisms, and animals as well as pathological tissue structures such as tumor cells, deposits in or on tissues, for example, arteriosclerotic plaque deposits, age pigments, etc. These structures are called "target structures" because these are the structures targeted for change either adding or removing a chosen type of lipid to or from the target system. The term "active ingredient system" means the combination of a lipid transfer protein and a lipid source or depot so that the lipid transfer protein can either transfer one type of lipid to the target system or from the target system or exchange lipids by transfer one type of lipid to the target system and removing a different type of lipid from the target system.

SUMMARY AND OBJECTS OF THE INVENTION

In view of the foregoing limitations and shortcomings of the prior art systems, as well as other disadvantages not specifically mentioned above, it is a primary object of the invention is to select and provide a protein for the specific and efficient targeted lipid exchange between a variety of target structures and the lipid component of the active ingredient system whereby the desired lipid is either removed or added to the target structure.

Briefly described, the aforementioned object is accomplished according to the invention by selecting an appropriate lipid transfer protein and lipid component to form an active ingredient system. The selection of the lipid transfer protein and lipid component to form the active ingredient system will depend on what desired effect on the target system is desired. With the foregoing and other objects, advantages and features of the invention that will become hereinafter apparent the nature of the invention may be more clearly understood by reference to the following detailed description of the invention and the appended claims.

DETAILED DESCRIPTION OF THE PREFERRED INVENTION

In the active ingredient system according to the invention, a transfer is described that is an entirely different basic process than a membrane fusion process as understood in membrane biophysics. In the active ingredient system according to the invention, a targeted modification of target structure is possible at the molecular level through the catalytic transfer of single lipid molecules. Lipid molecules of the type, which cannot form a membrane themselves, such as cholesterol, cannot even be transferred by the membrane fusion described earlier, but can be transferred in the active ingredient system according to the invention. The cholesterol would be part of a suitable lipid depot and a non-specific lipid transfer protein would be added to the lipid to form the active ingredient system. The active ingredient system would then be added to the desired target system and the lipid transfer protein would then transfer cholesterol to the target system. To remove cholesterol from a target system one would add an active ingredient system comprising a non-specific lipid transfer protein and a cholesterol free lipid depot. The lipid transfer protein would then transfer cholesterol from the target system to the lipid depot of the active ingredient system. The transfer of individual lipid species to the target structures in accordance with the invention does not take place by diffusion through the aqueous medium according to the laws of entropy, which would result in long transfer time periods and low transfer yields due to the low number of individual lipid molecules in an aqueous medium, but rather is accelerated by the use of the catalytic lipid transfer proteins of the lipid transfer system according to the invention. Because these proteins are components of the transfer system, they are able to act as catalysts to the transfer. By catalytic what is meant is that the lipid transfer protein can rapidly shuttle lipid or lipophilic drug from the active ingredient system, whether it be a liposome, emulsion, micelle or lipoprotein to a target structure which could be the outer surface of the skin, a tissue, a cell, cellular organelle, bacterium or fungus. This catalytic shuttle can also work in the reverse direction, for example, the transfer protein can rapidly shuttle cholesterol from an arteriosclerotic plaque deposit, which would be the target structure, to a liposome or micelle, the active ingredient system, for eventual metabolism or excretion as was discussed above. The lipid transfer proteins, as found in the aqueous medium and containing the lipid components within the aqueous media, can transport lipids or lipophilic compounds through the aqueous medium in order to transfer the lipids or lipophilic compounds to a target structure.

In one example of the transfer system the lipid supply accompanying the transfer protein can be present as an emulsion with the lipid transfer protein being present in the aqueous phase between the lipid droplets, while in a fusion system, only membranes themselves can be used as the lipid components. Furthermore, transfer proteins are unsuitable components for fusion processes. The lipid transfer system according to the invention is incompatible with fusion systems, both on the lipid side since lipid molecules are transferred individually and on the protein side since the lipid transfer proteins do not facilitate a fusion process.

The lipid transfer system also allows individual lipid or lipophilic molecules to be extracted from a target. The lipid or lipophilic molecules are then transferred to, for example, micelles for eventual excretion or metabolism.

Lipophilic or amphophilic components, such as lecithin, sphingomyelin, cholesterol, phosphatidylserine, phosphatidylethanolamine, phosphatidylglycerol, phosphatidylinositol, ganglioside, cerebroside, fat soluble vitamins and their derivatives, triglycerides, etc., and other lipids which can form the active ingredient system with one or more lipid transfer proteins, are transferred or exchanged with the target structures. The lipid components in the active ingredient system can be present in various forms, such as liposomes, micella, aerosols, emulsions, etc.

To form the active ingredient system as an aerosol, the desired lipid and an emulsifying compound are mixed and emulsified with water and an appropriate lipid transfer protein. The aerosol then can be used for lipid replacement therapy in the lungs, bronchial and nasal passages, or on the skin and mucous membranes.

To form an active ingredient system with emulsions, the desired lipid and an emulsifying compound are mixed, and the mixture is emulsified with an appropriate lipid transferring protein in water. The active ingredient system of the lipid transfer protein and emulsified lipid can then be used as a surfactant replacement to rebuild the lipid bilayer on the skin or mucous membranes. If a lipid transfer protein that is capable of transferring a lipophilic or amphophilic drug is used and the same lipophilic or amphophilic drug is then used with the emulsion, the emulsion can then act as a drug carrier. The active ingredient system of a lipid transfer protein and an emulsion can also be used in intravenous nourishment therapy. The advantages of this system are that lipids give twice the caloric energy per gram compared to carbohydrates. A problem that the use of lipid transfer proteins with an emulsion overcomes is the poor absorption of lipid emulsions in intravenous nutrition therapy.

To form the active ingredient system with micelles, membrane lipids which are lipids with the appropriate hydrophilic and hydrophobic molecular regions are added to an aqueous lipid transfer protein solution. The micelles can be used in a similar manner as the liposomes are used in an active ingredient system.

To form the active ingredient system with liposomes, membrane lipids, as defined above, are used to form liposomes by the following well known methods: detergent dialysis, extrusion microemulsification, high pressure homogenization or ultrasonic methods. In the detergent dialysis method, a mixture of lipid and detergent is dissolved in an aqueous lipid transfer protein solution and the detergent is subsequently removed by dialysis. In the extrusion process, a pure lipid is mixed with aqueous lipid transfer protein solution and the mixture passed through membranes of decreasing sort size. In the microemulsification process, pure lipid is mixed with an aqueous lipid transfer protein solution and the solution is then recirculated through an interactive chamber under high pressure.

The micelles and liposomes with the lipid transfer proteins as the active ingredient systems can be used on the skin, mucous membranes and in the blood as drug carriers, to repair membrane defects by transferring lipids to the defective membrane, for the storage of lipid material and as a depot for lipids that are extracted from target systems.

For the transfer or the exchange of the lipophilic or amphophilic components to the target structure, the active ingredient system is brought into contact with the target structure and the lipid exchange protein is allowed to shuttle lipid to and from the target structure.

The advantages that can be achieved with this invention lie in the targeted alteration of structure and function of complex associations of lipophilic and amphophilic components, such as membranes, tissues, micella, emulsions, cells, organelle, bacteria, viruses, parasites, tissue deposits, etc.

The invention also consists of the process of determining what the target structure is or will be and what lipid will be added, exchanged or removed from the target; selecting an appropriate lipid transfer protein to transfer the desired lipid and providing a lipid depot to serve either as a lipid source for transfer of lipid to the target structure or as a storage and transport facility for the storage or transport of lipid from the target structure.

Sources for the lipophilic or amphophilic components intended for the transfer or exchange are known to a person skilled in the art. They are either based on isolation from natural sources, such as plant or animal sources, based on chemical synthesis, or based on biotechnological methods from microbial sources.

Sources for the proteins that support the exchange or transfer of the lipid components are also known to person skilled in the art. The proteins can be used with different specificity through isolation from natural sources such as animal tissue, plants or through synthesis based on gene technology. The discussion in the previous section of this application of how different lipid transfer proteins have been isolated shows the level of knowledge in this art. An example of the isolation of a lipid transfer protein, as is known in the art, can take place according to the following general method:

1. tissue disintegration
2. centrifugation
3. ultra centrifugation at 100,000×G of the supernatant
4. precipitation of accompanying proteins through for example: acid or ammonium sulfate
5. dialysis
6. gel filtration
7. ion exchange chromatography
8. chromatofocussing In order to obtain lipid transfer systems as aerosols: lipids, lipid transfer proteins in an aqueous solution and additive compounds used as emulsifiers are emulsified and dispersed to form an aerosol. In order to obtain lipid transfer systems as an emulsion, additives are added to the lipid transfer proteins in aqueous solution during the emulsification of the lipids. In order to obtain the lipid transfer system as micella, the lipids are added as a pure substance to an aqueous lipid transfer protein solution.

In order to obtain lipid transfer systems as liposomes, detergent dialysis or extrusion or microemulsification as well as high pressure homogenization or ultrasonic methods are used. In detergent dialysis, the non-aqueous mixture of lipid and detergent is absorbed into an aqueous lipid transfer protein solution and the detergent is subsequently removed by dialysis.

In the extrusion, pure lipid is absorbed in an aqueous lipid transfer protein solution and this mixture is pressed through membranes of decreasing pore size.

In the microemulsification method, pure lipid is absorbed in an aqueous lipid transfer protein solution and is recirculated through an interaction chamber under high pressure.

The active ingredient system according to the invention can be obtained as follows:

A lipid transfer protein with a suitable specificity for phospholipids is isolated from tissue, in particular lipid transfer proteins isolated from cattle brains are preferred. An aqueous solution of the lipid transfer protein was mixed with a suitable lipid component, such as phosphatidyl-choline, and with a 5 fold excess of lipid. The mixture is converted into an emulsion by a suitable technique, such as high pressure homogenization, microfluidization, etc. An aliquot part of this emulsion is added to an aqueous suspension of unilamellar liposomes and the transfer activity is measured by suitable methods, such as fluorescence techniques or radioactivity. The standardized transfer system thus becomes capable of application.

The lipid transfer protein systems in both cases assure a rapid exchange of the lipids between the lipid components and the target structure.

Lipid transfer systems of this type can be used in place of membranes for the transfer of lipids. Accordingly, through a comparative analysis of the lipid proportion exchanged through the lipid transfer protein and the total lipid of a lipid membrane, an asymmetrical distribution of lipids in the bilayer of the target structure can be determined. In labeling the membrane, lipids that are marked either radioactively, with fluorescence labels, or ESR and NMR labels are built into the membrane structures with the aid of the lipid transfer system as the lipid transfer protein transfers the labeled lipids from the active ingredient system to the target system or vice versa.

Asymmetrical distributions of lipids can be produced in natural or artificial membrane bilayer structures through the use of lipid transfer systems. A specific composition of lipids (membrane engineering) made from natural or artificial membranes can be obtained through extraction of lipids to the active ingredient system.

In a stabilization process, active ingredient systems with lipid transfer proteins can stabilize natural and artificial cells, organelles or membrane structures, such as liposomes, because the active ingredient system eliminates membrane defects through the addition of lipids from the lipid component to the active ingredient system to the target system to be stabilized through the action of the lipid transfer protein.

The active ingredient system can be used in technology to maintain or to build up a lipid monolayer on materials, for example, a sliding film, or to prevent direct aqueous wetting of a surface, or to improve the biocompatibility of boundary surfaces. In cosmetics, the active ingredient system serves to reorganize membrane structures in the skin that have been functionally damaged or altered, just as it can in dermatology.

In medicine, the active ingredient system can be used as a medication carrier (drug carrier) to stabilize liposomes relative to blood components. An additional application in medicine is that the active ingredient system is used to produce asymmetrical liposomes for a targeted application of medication (drug targeting). Especially significant is the use of the active ingredient system in handling arteriosclerosis, through which the cholesterol in an arteriosclerotic plaque is extracted. For this purpose, cholesterol-free liposomes as the lipid component, are employed in connection with lipid transfer proteins.

An additional application of the active ingredient systems lies in the handling of disturbances in the lipid material exchange. Thus, for example, lipid transfer systems can be used to regulate bile acid synthesis.

The active ingredient system can be contained in various products in technology, medicine or cosmetics. Thus, for example, the active ingredient system can be included in a salve, creme, gel or spray.

With the active ingredient system according to the invention the evaporation barrier of human and animal skin can be built up. This evaporation barrier of the skin is located in the horny stratum and comprises a complex structure of lipid membranes. This complex structure consisting of multilamillar lipid formations can be partially or totally destroyed by harmful mechanical, thermal, chemical, radiological or micro-biological damage. This damage to the lipid membranes often leads to life threatening conditions as water is lost to the surrounding air.

The active ingredient system of this invention can be used to build up the lipid membrane of the skin after such damage. A desired active ingredient system would comprise a lipid transfer protein capable of transferring glycolipids and a lipid source comprising glucolipids and other skin lipids in the form of an emulsion to be applied to the skin at the desired location.

An example of a lipid component which is favorably used is a glycolipid which exits in natural skin structures and which normally builds the evaporation barrier. Gluco- and galactocerebrosides are preferred glycolipids which can be isolated out of natural products or are commercially available.

The lipid component per se is not capable of building up the evaporation barrier because the necessary incorporation of the lipid components in the complex structure of the dermal evaporation barrier is too slow. However, with the active ingredient system according to the invention, a catalytic and accelerated incorporation of the lipids and the rebuilding of the skin evaporation barrier is made possible.

EXAMPLE 1

For such an active ingredient system the lipid transfer protein is extracted out of cattle brain as follows:

Cattle brain is freshly homogenized and ultra-centrifuged at 100,000×G the supernatant is decanted and lyophilized. The lyophilized material is taken up in a buffer and is chromatographed on phenylsepharose. The protein fraction with a molecular weight between 20 and 30 kd of the protein fraction is recovered and further purified by chromatofocussing.

The thus obtained water soluble protein component(s) and the lipid component(s) are combined to create the lipid transfer system. For the synthesis of the dermal evaporation barrier the active ingredient system is used, for example, as a liposomal hydrogel. The liposomal hydrogel is formed from addition of the lipid transfer protein to a liposomal suspension of gluco-lipids to form the active ingredient system.

The incorporation of the lipid component(s) in the target structure—in this case in the form of a membrane—is enhanced by a factor of 100 to 1,000, if the active ingredient system according to the invention is used compared to the use of only the lipid component(s), as a rebuild substance for the evaporation barrier of natural skin.

EXAMPLE 2

The catalytic transfer of D-α-tocopherol is described in this Example. The lipid transfer protein was isolated from beef liver.

The beef liver lipid transfer protein was isolated by the following process. Freshly slaughtered beef liver was pulverized with a mortar in liquid nitrogen. A homogenate of 1:5 (W/V) liver to buffer was prepared with a HEPES buffer and the homogenate was further homogenized in a Douce homogenizator. The homogenate was then centrifuged at 4,000×g for 15 minutes and the supernatant decanted. The supernatant was then ultra-centrifuged at 100,000×g for ninety minutes and the desired transfer protein is found in the supernatant. The supernatant is subjected to a two-stage ammonium sulfate precipitation.

A 40% solution (22.6 gm of ammonium sulfate per 100 ml solution) was slowly added to the supernatant. The solution was stirred for 12 hours before being centrifugated at 14,000×g for 15 minutes. The pellet was discarded and the supernatant was used in the 90% ammonium sulfate precipitation.

A 90% ammonium sulfate solution (33.5 gm of ammonium sulfate per 100 ml solution) was added to the supernatant with stirring. The supernatant was then centrifugated at 14,000×g and the pellet was suspended in a small amount of MOPS buffer and dialyzed against the MOPS buffer for twenty four hours. The flocculent precipitate resulting from dialysis is pelletized at 14,000×g for 15 minutes. The pelletized protein was then used without further purification.

Liposomal test systems were prepared so that the D-α-tocopherol containing liposomes had an average size range of 220–230 nm in diameter. The D-α-tocopherol free liposomes were 70–80 nm in diameter and the different sized liposomes can be separated from one another by centrifugation and the D-α-tocopherol concentration in the supernatant 70–80 nm liposomes, can be determined by high performance thin layer chromatography, "HPTLC", and the amount of D-α-tocopherol transferred quantified.

The experiments showed that the isolated beef liver lipid transferase had a specific activity of 23.168 I.U. and that D-α-tocopherol can be transferred from an enriched liposome of one size to a D-α-tocopherol free liposome of a different size.

The active ingredient system of the present invention can now be used to transfer D-α-tocopherol to skin or other lipid membranes by applying the active ingredient system with the lipid portion being in the form of an emulsion, liposomes or micells directly to the skin or optionally with a conventional emulsion carrier.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method for treating the skin comprising selecting a lipid to incorporate into the lipid layer of the skin, selecting a lipid transfer protein or mixture of lipid transfer proteins that can transfer the selected lipid, forming an active ingredient system by combining an aqueous solution of said lipid transfer protein with said lipid, and topically applying said active ingredient system to the skin.

2. The method of claim 1 wherein the lipid mixture is in a form selected from the group of emulsions, micelles, liposomes and aerosols.

3. The method of claim 2 wherein the lipid to be transferred is selected form the group of fat soluble vitamins comprising vitamins A, D, E, K and carotenoids.

4. The method of claim 3 wherein the lipid to be transferred is D-α-tocophenol.

5. The method of claim 1 wherein, the lipid to be transferred is selected from the group of fat soluble vitamins comprising vitamins A, D, E, K and carotinoids.

6. The method of claim 2 wherein the lipid to be transferred is a phospholipid.

7. The method of claim 6, wherein the phospholipid is selected from the group consisting of phosphatidylserine, phosphatidylethanolamine, phosphatidylglycerol and phosphatidylinositol.

8. The method of claim 1, wherein the lipid to be transferred is a glycolipid.

9. The method of claim 8, wherein the glycolipid is selected from the group consisting of gangliosides, glucocerebrosides and galactocerebrosides.

* * * * *